(12) United States Patent
Yano et al.

(10) Patent No.: US 9,346,849 B2
(45) Date of Patent: May 24, 2016

(54) AMINO SUGAR-BOUND ANTI-CANCEROUS NOBLE METAL COMPLEX

(71) Applicant: NATIONAL UNIVERSITY CORPORATION NARA INSTITUTE OF SCIENCE AND TECHNOLOGY, Ikoma-shi, Nara (JP)

(72) Inventors: Shigenobu Yano, Ikoma (JP); Takashi Shibahara, Okayama (JP); Shunichiro Ogura, Yokohama (JP)

(73) Assignee: NATIONAL UNIVERSITY CORPORATION NARA INSTITUTE OF SCIENCE AND TECHNOLOGY, Ikoma-Shi, Nara (JP)

( * ) Notice: Subject to any disclaimer, the term of this patent is extended or adjusted under 35 U.S.C. 154(b) by 0 days.

(21) Appl. No.: 14/375,027

(22) PCT Filed: Jan. 29, 2013

(86) PCT No.: PCT/JP2013/051843
§ 371 (c)(1),
(2) Date: Jul. 28, 2014

(87) PCT Pub. No.: WO2013/115157
PCT Pub. Date: Aug. 8, 2013

(65) Prior Publication Data
US 2014/0378402 A1 Dec. 25, 2014

(30) Foreign Application Priority Data
Jan. 30, 2012 (JP) ................. 2012-016735

(51) Int. Cl.
A01N 55/02 (2006.01)
A61K 31/28 (2006.01)
C07H 23/00 (2006.01)
C07H 15/26 (2006.01)

(52) U.S. Cl.
CPC ............... *C07H 23/00* (2013.01); *C07H 15/26* (2013.01)

(58) Field of Classification Search
None
See application file for complete search history.

(56) References Cited

U.S. PATENT DOCUMENTS 5,021,567 A 6/1991 Johnson et al.
5,118,499 A 6/1992 Theodoropulos

OTHER PUBLICATIONS

International Search Report for PCT/JP2013/051843 dated Feb. 18, 2013.
Synth.React.Inorg.Met.-Org.Chem., 2000, vol. 30, No. 1, pp. 1-17.
Bulletin of the Chemical Society of Japan, 1972, vol. 45, No. 2 pp. 477-481.
Sachinvala, N.D. et al., J.Med.Chem., 1993, vol. 36 pp. 1791-1795.
Tsubomura, T. et al., Inorganic Chemistry, 1990, vol. 29, No. 14, pp. 2622-2626.
Hanessian, S. et al., Canadian Journal of Chemistry, 1993, vol. 71, pp. 886-895.
Chen & Y et al. Angewandte Chemie International Edition, 1999, vol. 38, No. 12, pp. 1768-1769.
Ackley, M.C. et al., Journal of Biological Inorganic Chemistry, 2004, vol. 9, pp. 453-461.
Zhang, J. et al., Journal of Medicinal Chemistry, 2003, vol. 46, No. 16, pp. 3502-3507.
Yan, L. et al., Journal of Inorganic Biochemistry, 2012, vol. 106, pp. 46-51.
Price J.H. et al., Inorganic Chemistry, 1972, vol. 11, No. 6, pp. 1280-1284.
Abstracts of the 39th Symposium on Main Group Element Chemistry, 2012, pp. 77-80.
Abstracts of the 92nd Annual Meeting of the Chemical Society of Japan, 2012, p. 488, 3 F7-46.
Abstracts of the 61st JSCC Symposium, 2011, p. 168, 3E-13.
Abstracts of the 62nd JSCC Symposium, 2012, p. 116, 2E-08.

*Primary Examiner* — Patrick Lewis
(74) *Attorney, Agent, or Firm* — Stephen J. Weyer, Esq.; Stites & Harbison, PLLC

(57) ABSTRACT

Disclosed is a pharmaceutical composition containing as an active ingredient a compound represented by formula (I) or a physiologically acceptable salt thereof, and a method for treating cancer, the method including administering the compound represented by formula (I) or the physiologically acceptable salt thereof.

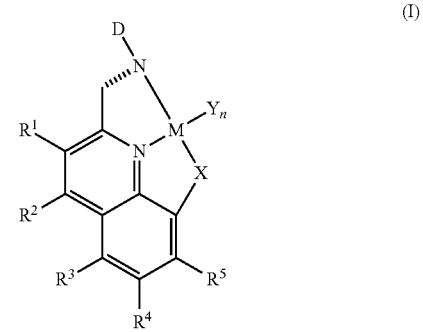

(I)

14 Claims, 4 Drawing Sheets

AMINO SUGAR-BOUND ANTI-CANCEROUS NOBLE METAL COMPLEX

TECHNICAL FIELD

The present invention relates to a novel pharmaceutical composition that has excellent antitumor activity, and to a method for treating cancer.

BACKGROUND OF THE INVENTION

Cisplatin, a long-known anticancer agent, has a four-coordinate square planar, very simple structure in which ammonia molecules and chloride ions are coordinated to divalent platinum in a cis-configuration. This anticancer agent is useful and continues to be used in clinical practice today.

Following cisplatin, a variety of anticancer agents have been developed. In Japan, carboplatin, nedaplatin, and oxaliplatin have been used in clinical applications.

Metal complexes, which comprise a metal ion and one or more organic substances, provide a potential for elucidating the role and biological mechanism of trace metal ions, which are essential for life activity, and have thus had a significant impact on recent development in bioscience. Research on the behavior of metal ions in animals and humans, and on the benefits of metal ions as a medical drug, was initiated already several decades ago. Chemists, pharmacologists, and medical scientists have collaborated and developed a new academic field, namely, inorganic pharmacology.

Sugar plays in vivo a vital role for life activity, such as in energy storage, structure-building materials, and molecular recognition, as well as an energy source. Chitin and chitosan are polymeric glucosamine into which amine is introduced, and thus have increased coordinating power as compared with glucose. Chitin and chitosan are the major components of crustacean exoskeletons, and the most abundant after cellulose. Despite the fact that glucosamine is such an essential sugar, there are limited reports about complexes containing glucosamine as a ligand. In particular, there are few reports on noble metal complexes containing glucosamine as a ligand.

Non-patent Documents 1 to 4 report on novel platinum complexes that have various sugar backbones. The platinum complexes disclosed in these documents have a structure in which the platinum atom is coordinated with two chloride ions or two iodide ions.

Non-patent Document 1 reports on the synthesis and antitumor activity of platinum(II) diamino sugar complexes. Non-patent Document 2 reports that mono and dihydroxy diamino tetrahydropyran derivatives were prepared and converted into the corresponding diamino cis-platinum analogs, and that their antitumor activity was evaluated. Non-patent Document 3 reports on the synthesis and antitumor activity of platinum complexes containing one or more platinum centers bound to sucrose-derived ligands. Non-patent Document 4 reports on the synthesis and cytotoxicity of a carbohydrate-linked cisplatin analogue.

Non-patent Documents 5 to 7 disclose platinum or palladium complexes that have a structure in which the metal atom is coordinated with three atoms (N and S) and one chloride ion. Non-patent Document 8 reports on the synthesis of DMSO complexes of platinum(II) and palladium(II).

CITATION LIST

Non-Patent Document

Non-patent Document 1: Tsubomura, T. et al., Inorg. Chem. 1990, 29, 2622-2626
Non-patent Document 2: Hanessian, S. et al. Can. J. Chem. 1993, 71, 886-895
Non-patent Document 3: Sachinvala, N. D. et al., J. Med. Chem. 1993, 36, 1791-1795
Non-patent Document 4: Chen and Y. et al., Angew. Chem. Int. Ed. 1999, 38, 1768-1769
Non-patent Document 5: Ackley, M. C. et al., J. Biol. Inorg. Chem. 2004, 9, 453-461
Non-patent Document 6: Zhang, J. et al., J. Med. Chem. 2003, 46, 3502-3507
Non-patent-Document 7: Yan, L. et al., J. Inorg. Biochem. 2012, 106, 46-51
Non-patent Document 8: Price, J. H., et al., Inorg. Chem. 1972, 11, 1280-1284

SUMMARY OF INVENTION

Technical Problem

However, anticancer agents such as the cisplatin mentioned above have disadvantages, including poor water solubility and serious side effects of the agents. Moreover, these agents pose problems such as continuous usage of the same type of anticancer agent causing the cancer to acquire resistance to the agent. For this reason, development of novel anticancer agents is eagerly awaited.

Another problem is that the synthesis of the platinum complexes as disclosed in Non-patent documents 1 to 7 is complicated. Moreover, no cases are known of a sugar-linked platinum or palladium complex that has a structure in which the metal atom is coordinated with three atoms, i.e., N, O, and S, with one chloride ion.

An object of the present invention is to provide a novel pharmaceutical composition that contains an easily synthesized drug and that exhibits excellent biocompatibility and antitumor activity.

Solution to Problem

The present inventors neutralized naturally occurring, highly biocompatible D(+)-glucosamine hydrochloride, and reacted it with 8-hydroxy-2-quinolinecarbaldehyde (HOqn) to thereby synthesize a novel Pd (II) complex [PdCl(GlcN=qnO)] containing a Schiff base (GlcN=qnO=N-(8-hydroxyquinoline-2-ylmethylidene)-β-D-glucosamine) as a ligand. Thereafter, they conducted the characterization and X-ray crystal structural analysis of the Pd complex, and found that the Pd complex has significantly higher anticancer activity ($IC_{50}$), which is about two to five times higher than that of cisplatin (CDDP), against stomach cancer cells MKN45 and MKN28.

The present invention, accomplished on the basis of these findings, provides the following pharmaceutical compositions, method, and use.

Item 1. A pharmaceutical composition containing as an active ingredient a compound represented by formula (I) or a physiologically acceptable salt thereof,

[Chem. 1]

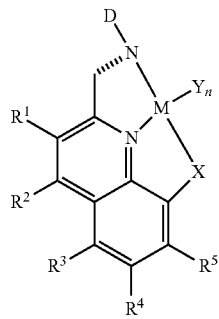
(I)

[Chem. 2]

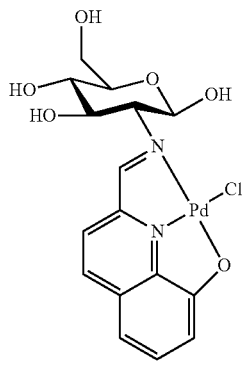
(II)

wherein the symbol "⦀" denotes a single bond "—" or a double bond "═";

$R^1$ to $R^5$ are the same or different, and each represents hydrogen, alkyl, hydroxyalkyl, alkoxy, hydroxy, halogen, nitro, amino, a sugar residue, or a luminescent pigment;

M represents palladium, platinum, gold, iridium, or ruthenium;

X represents —O—, —NH$_2$—, —S—, —SH—, or —OSO$_2$—;

Y represents halogen or a long-chain fatty acid residue;

D represents a monosaccharide residue, an oligosaccharide residue, or a sugar-linked polyethylene glycol residue; and n represents an integer of 0 to 3.

Item 2. The pharmaceutical composition according to Item 1, wherein $R^1$ to $R^5$ represent hydrogen.

Item 3. The pharmaceutical composition according to Item 1 or 2, wherein M is palladium or platinum.

Item 4. The pharmaceutical composition according to any one of Items 1 to 3, wherein D is a glucose residue, a galactose residue, or a mannose residue.

Item 5. The pharmaceutical composition according to any one of Items 1 to 4, wherein D is a D(+)-glucose residue.

Item 6. The pharmaceutical composition according to Item 5, wherein the D(+)-glucose residue is a β-D(+)-glucose residue.

Item 7. The pharmaceutical composition according to any one of Items 1 to 4, wherein D is an L(−)-glucose residue.

Item 8. The pharmaceutical composition according to Item 7, wherein the L(−)-glucose residue is a β-L(−)-glucose residue.

Item 9. The pharmaceutical composition according to any one of Items 1 to 8, wherein X is —O—.

Item 10. The pharmaceutical composition according to any one of Items 1 to 9, wherein Y is halogen.

Item 11. The pharmaceutical composition according to any one of Items 1 to 10, wherein Y is chlorine.

Item 12. The pharmaceutical composition according to any one of Items 1 to 11, wherein M is palladium.

Item 13. The pharmaceutical composition according to any one of Items 1 to 6, and 9 to 12, wherein the compound represented by formula (I) is a compound represented by formula (II).

Item 14. The pharmaceutical composition according any one of Items 1 to 13, which is an anticancer agent.

Item 15. A method for treating cancer, the method comprising administering the compound represented by formula (I) or the physiologically acceptable salt thereof according to Item 1.

Item 16. Use of the compound represented by formula (I) or the physiologically acceptable salt thereof according to Item 1 for producing an anticancer agent.

Item 17. The compound represented by formula (I) or the physiologically acceptable salt thereof according to Item 1 for use in the treatment of cancer.

Advantageous Effects of Invention

The pharmaceutical composition according to the present invention is a novel pharmaceutical composition that shows excellent biocompatibility and antitumor activity. Further, the compound contained in the pharmaceutical composition according to the present invention can be synthesized using a very simple method, and one-pot synthesis is also possible.

Furthermore, when synthesizing the compound to be contained in the pharmaceutical composition of the present invention, the type of amino sugar and the type of metal may be easily selected; thus, the present invention is expected to contribute to the synthesis of a compound useful against resistant cancer.

DESCRIPTION OF EMBODIMENTS

Figure 1:
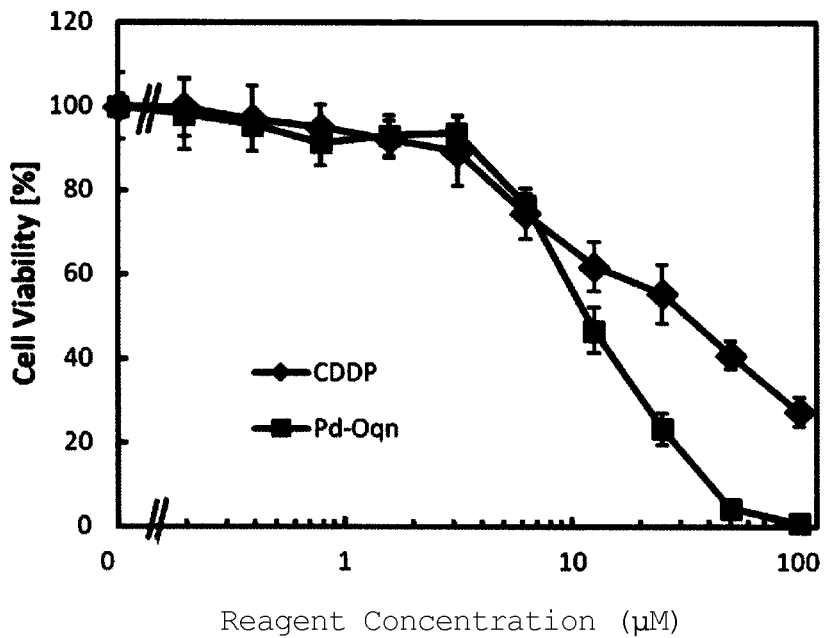
FIG. 1 is a graph showing the evaluation results of the toxicity of CDDP and Pd-Oqn to MKN45.
Figure 2:
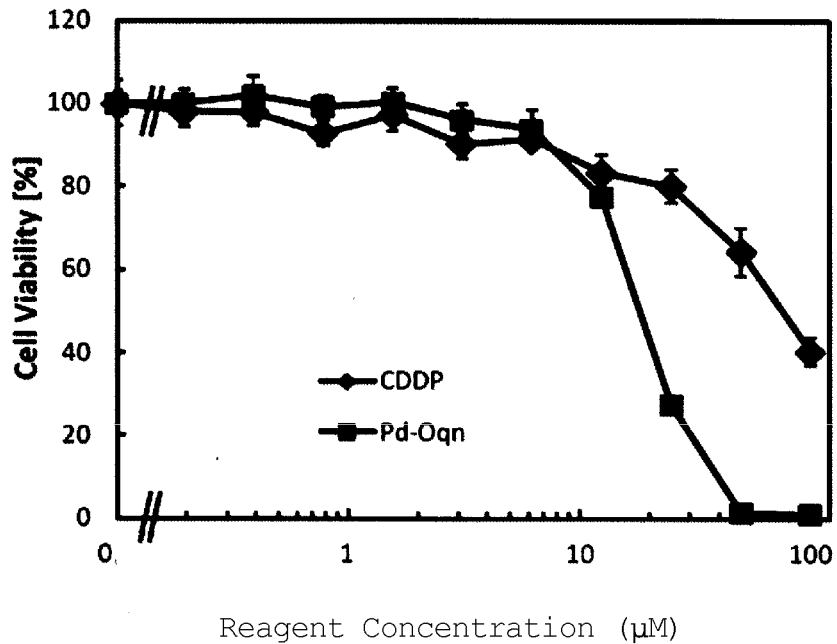
FIG. 2 is a graph showing the evaluation results of the toxicity of CDDP and Pd-Oqn to MKN28.
Figure 3:
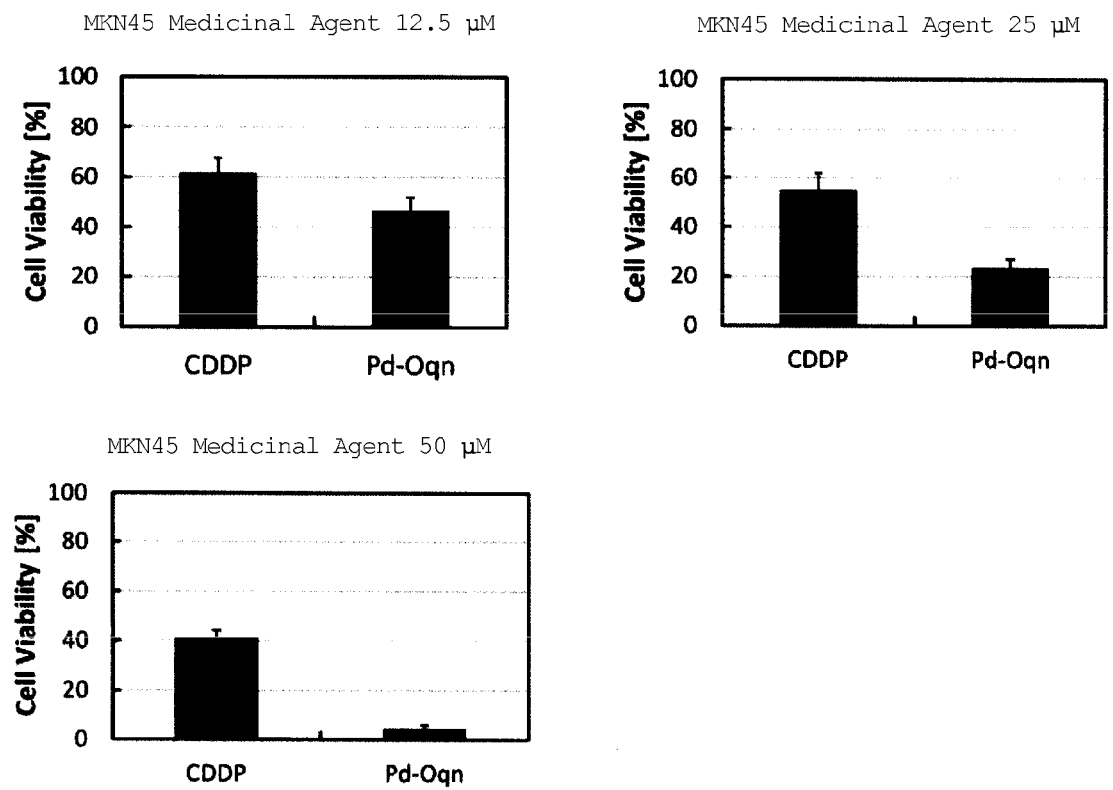
FIG. 3 is a graph showing the evaluation results of the toxicity of CDDP and Pd-Oqn to MKN45.
Figure 4:
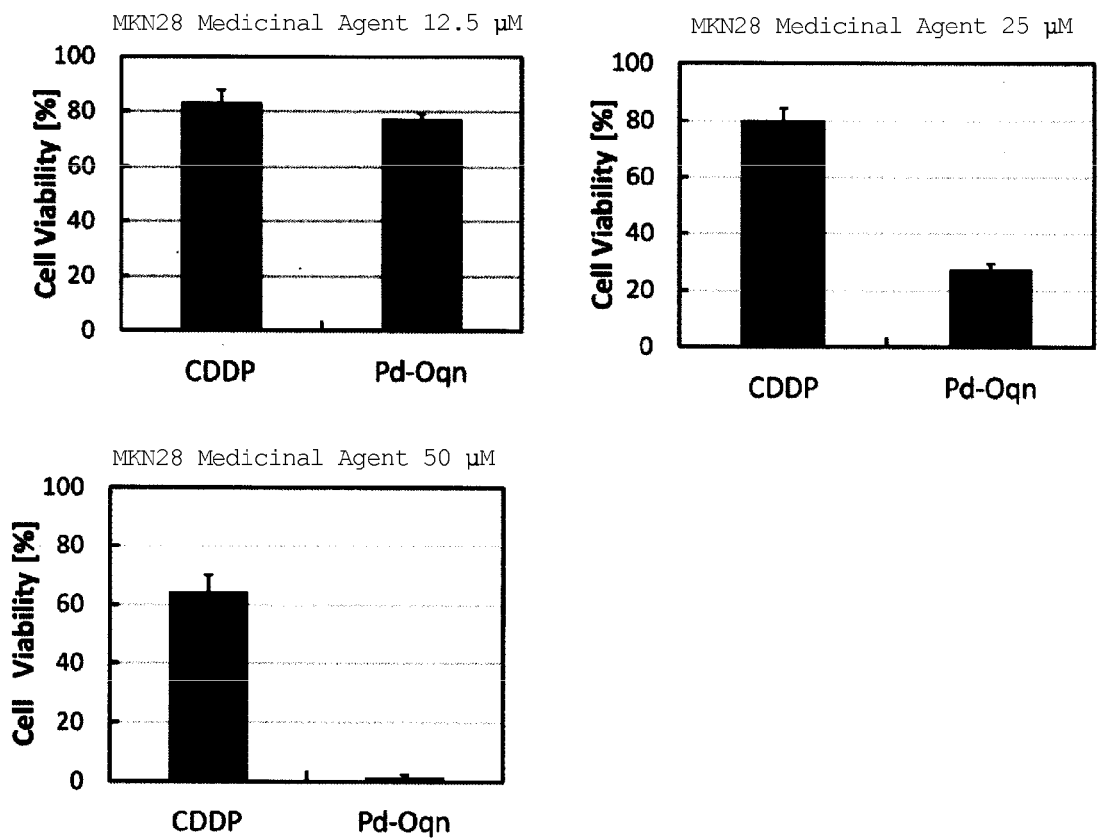
FIG. 4 is a graph showing the evaluation results of the toxicity of CDDP and Pd-Oqn to MKN28.

The following describes the present invention in detail.

The pharmaceutical composition according to the present invention is characterized in that it contains as an active ingredient a compound represented by formula (I) or a physiologically acceptable salt thereof,

[Chem. 3]

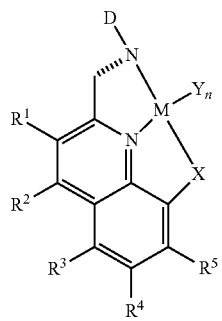
(I)

wherein the symbol "||||||" denotes a single bond "—" or a double bond "=";

$R^1$ to $R^5$ are the same or different, and each represents hydrogen, alkyl, hydroxyalkyl, alkoxy, hydroxy, halogen, nitro, amino, a sugar residue, or a luminescent pigment;

M represents palladium, platinum, gold, iridium, or ruthenium;

X represents —O—, —NH$_2$—, —S—, —SH—, or —OSO$_2$—;

Y represents halogen or a long-chain fatty acid residue;

D represents a monosaccharide residue (preferably, a glucose residue, galactose residue, or mannose residue), an oligosaccharide residue, or a sugar-linked polyethylene glycol residue; and n represents an integer of 0 to 3.

Preferably, $R^1$ to $R^5$ are hydrogen or amino, with hydrogen being more preferable. Preferably, M is palladium or platinum.

Preferably, D is a D(+)-glucose residue or an L(−)-glucose residue. More preferably, D is a β-D(+)-glucose residue or β-L(−)-glucose residue.

Preferably, D is selected from the following group.

[Chem. 4]

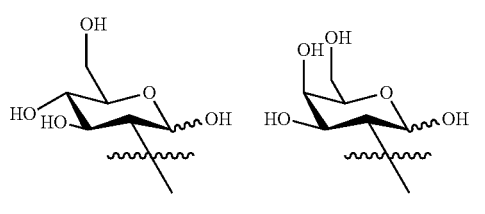

D(+)-glucose (D-Glc) residue    D(+)-galactose (D-Gal) residue

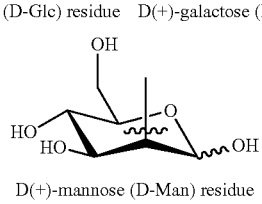

D(+)-mannose (D-Man) residue

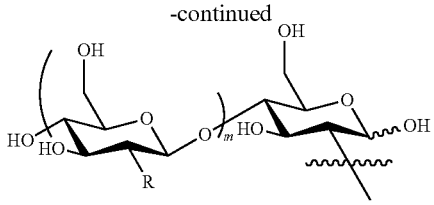

R = OH or NH$_2$

Oligosaccharide (M = 1 to 9) residue

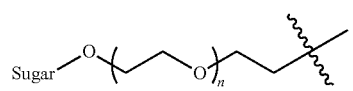

Sugar = D-Glc, D-Man or D-Gal

Sugar-linked PEG (polyethyleneglycol, n = 1 to 2,500) residue

Alkyl may be linear or branched, and is preferably $C_{1-6}$ alkyl, with $C_{1-3}$ alkyl being more preferable. Examples of alkyl groups include methyl, ethyl, n-propyl, isopropyl, n-butyl, isobutyl, tert-butyl, n-pentyl, isopentyl, and hexyl. Here, the definition of alkyl is also applied to the alkyl portions of hydroxyl alkyl and alkoxy. Examples of sugar residues include monosaccharide residues, oligosaccharide residues, and polysaccharide residues, with monosaccharide residues and oligosaccharide residues being more preferable.

Examples of luminescent pigments include NB(N-(7-nitrobenz-2-oxa-1,3-diazol-4-yl)amine).

Preferably, the symbol "||||||" is a double bond "=". Preferably, X is —O—, and preferably, Y is halogen.

Examples of halogen include fluorine, chlorine, bromine, and iodine, with chlorine being preferable.

The long-chain fatty acid refers to a fatty acid having at least 12 carbon atoms. Examples include dodecanoic acid, tetradecanoic acid, pentadecanoic acid, and hexadecanoic acid.

Preferably, n is 1. When M is palladium or platinum, n=1. When M is gold, n=0 or 2. When M is iridium or ruthenium, n=1 to 3. When n=2, two Ys are bonded to M as shown below (in which case, two Ys are the same or different.) When n=3, three Ys are bonded to M as shown below (in which case, three Ys are the same or different).

[Chem. 5]

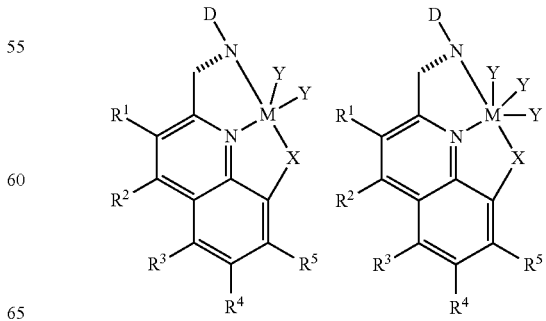

The compound represented by formula (I) is preferably a compound represented by formula (II).

[Chem. 6]

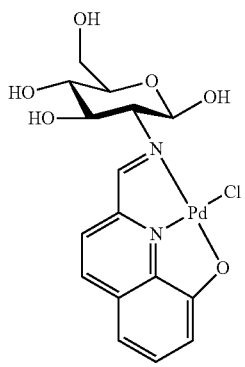

(II)

The physiologically acceptable salt of the compound represented by formula (I) is a physiologically acceptable acid addition salt or a salt with a base. Examples of acid addition salts include hydrochloride, sulphate, hydrobromide, perchlorate, phosphate, hydroiodide, oxalate, succinate, malonate, maleate, and glutamate. Examples of salts with bases include potassium salt, sodium salt, calcium salt, triethylamine salt, and pyridine salt.

The compound represented by formula (I) is produced by reacting a compound represented by the following formula (III) with, for example, an amino sugar (glucosamine, galactosamine, mannosamine), an amino-oligosaccharide, or a sugar-linked PEG amine, and reacting the resulting compound with a salt of a metal that corresponds to a desired central metal.

[Chem. 7]

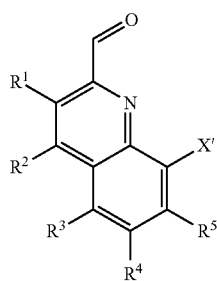

(III)

wherein X' represents hydroxy, amino, or thiol group.

The solvent used for the reaction of a compound represented by formula (III) with an amino sugar, an amino-oligosaccharide, or a sugar-linked PEG amine can be suitably selected depending on the type of the compound for use. Examples include methanol and ethanol. The solvent may be used singly or in combination. For this reaction, it is preferable to use about 1 mole of a compound represented by formula (III) per mole of an amino sugar, an amino-oligosaccharide, or a sugar-linked PEG amine. The reaction temperature and reaction time can also be suitably determined depending on the type of the compound for use, or the like. The reaction temperature is typically about 40° C., and the reaction time is typically about 20 hours. The reaction of the compound represented by formula (III) with an amino sugar, an amino-oligosaccharide, or a sugar-linked PEG amine gives a compound represented by the following formula (IV).

[Chem. 8]

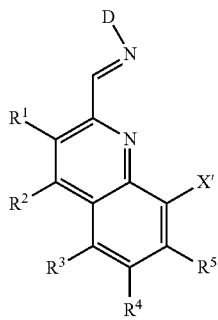

(IV)

Examples of metal salts used for the reaction with a compound represented by formula (IV) include $Na_2PdCl_4$ and $K_2PtCl_4$. The solvent used for the reaction of a compound represented by formula (IV) with a metal salt can be suitably selected depending on the type of the compound for use. Examples include methanol and ethanol. The solvent may be used singly or in combination. For this reaction, it is preferable to use 0.9 mole of a metal salt per mole of a compound represented by formula (IV). The reaction temperature and reaction time can also be suitably determined depending on the type of the compound for use, or the like. The reaction temperature is typically 10° C., and the reaction time is typically 0.2 hour.

The amino sugar (glucosamine, galactosamine, and mannosamine), amino-oligosaccharide, sugar-linked PEG amine, compound represented by formula (III), and metal salt, which are used as starting materials in the above production method, are readily available commercially, or can be produced following known methods.

The compound represented by formula (I) obtained through the above production method can be isolated and purified following a known procedure, such as crystallization, recrystallization, concentration, concentration under reduced pressure, solvent extraction, chromatography, distillation, fractional distillation, and phase transfer.

When the compound represented by formula (I) is obtained in a free form, crystals can be formed following a conventional method. The compound represented by formula (I), when obtained as a hydrate and alcoholate in the form of crystals, may be converted to a free form by using a conventional procedure.

As described above, commercially available amino sugar, amino-oligosaccharides, and aromatic aldehyde can be used as a starting material for the compound of the present invention. The synthesis method is also very simple, and one-pot synthesis is also possible. Furthermore, because the type of amino sugar and the type of metal may be easily selected in synthesis, a compound useful for resistant cancer is expected to be synthesized.

The pharmaceutical composition according to the present invention is preferably an anticancer agent. The "anticancer agent" according to the present invention is also referred to as an "antitumor agent," "antitumor medicament," "antitumor pharmaceutical composition," and the like.

The pharmaceutical composition according to the present invention is administered to a mammal, including a human.

The pharmaceutical composition according to the present invention may optionally contain a biologically acceptable carrier, excipient, and the like, depending on the dosage form. The anticancer agent according to the present invention can be produced in accordance with a conventional procedure. The agent may be administered, for example, orally as an optionally sugar-coated or enteric coated tablet, capsule, microcapsule, or elixir, administered percutaneously as a topical product, such as ointment or plaster, administered nasally as an aerosolized agent, administered transbronchially as an inhalant, or administered parenterally as an injectable drug, such as an aseptic solution or suspension containing water or another pharmaceutically acceptable solution.

Although the amount of the compound represented by formula (I), i.e., an active ingredient of the pharmaceutical composition of the present invention, is suitably determined depending on the dosage form, administration route, and the like, the amount is typically about 0.001 to 70 wt % based on the total amount of the drug product.

The dosage of the pharmaceutical composition of the present invention can be suitably determined ultimately at a physician's discretion, taking into consideration the type of dosage form, mode of administration, age and weight of the patient, symptoms of the patient, or the like.

Examples of cancers that may be treated by using the pharmaceutical composition of the present invention include stomach cancer, rectal cancer, colon cancer, hepatic cancer, pancreatic cancer, pulmonary cancer, pharyngeal cancer, esophageal cancer, renal cancer, gallbladder and bile duct cancer, head and neck cancer, bladder cancer, prostate cancer, breast cancer, uterine cancer, and ovarian cancer. In particular, the pharmaceutical composition of the present invention is expected to exert a potent effect on stomach cancer. Moreover, the pharmaceutical composition is expected to have an advantageous effect on drug-resistance tumors.

The pharmaceutical composition according to the present invention is a novel pharmaceutical composition with excellent antitumor activity and is expected to have tumor selectivity and lowered toxicity because of the amino sugar attached.

EXAMPLES

Hereinafter, the Examples will describe the present invention in detail. However, the present invention is not limited to the Examples.

Synthesis Example 1

[Chem. 9]

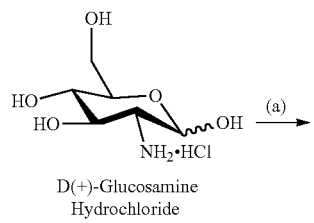

D(+)-Glucosamine Hydrochloride

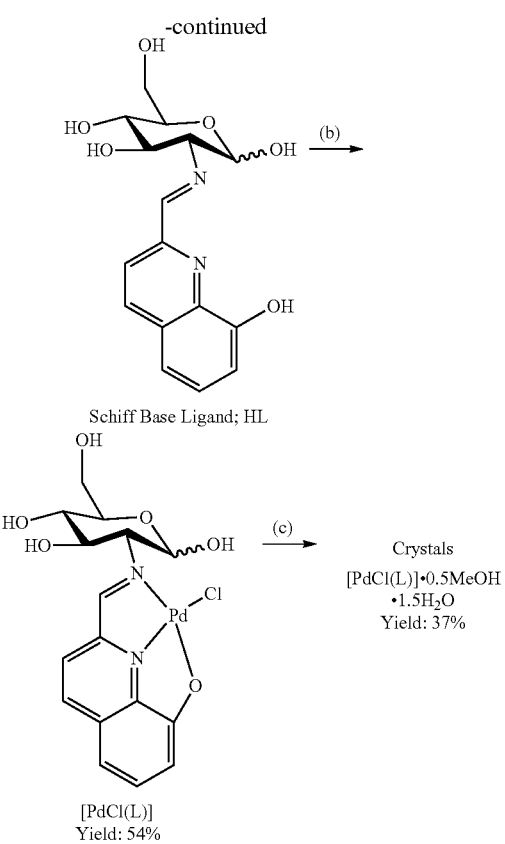

Schiff Base Ligand; HL

[PdCl(L)]
Yield: 54%

Crystals
[PdCl(L)]·0.5MeOH
·1.5H$_2$O
Yield: 37%

Condition: (a) tBuOK, 8-hydroxyl-2-quinolinecarbaldehyde/MeOH
(b) Column chromatography (SiO$_2$, MeOH), Na$_2$PdCl$_4$/MeOH
(c) recrystallization from DMF/MeOH HL: GlcN = qnOH, N-(8-hydroxy-quinoline-2-ylmethylidene)-β-D-glucosamine D(+)-glucosamine hydrochloride (156.13 mg, 0.72 mmol) was neutralized with potassium t-butoxide (80.65 mg, 0.72 mmol) in methanol (40 mL). 8-Hydroxy-2-quinolinecarbaldehyde (126.32 mg, 0.73 mmol) dissolved in methanol (20 mL) was added thereto, and the mixture was stirred at room temperature for 20 hours. The mixture was concentrated to a volume of about 5 mL on a rotary evaporator with heating on a water bath heated to about 40° C. Thereafter, the concentrate was developed through a silica gel column of 18×3 cm (developing solvent: methanol), and the colored layers were all recovered. Sodium chloropalladate(II) (202.76 mg, 0.67 mmol) dissolved in methanol (30 mL) was added thereto, and the system began to become turbid in about 5 seconds, thereby forming a precipitate of a black powder (crude yield: 184.84 mg, 54%).

The black powder was subjected to DMF/methanol vapor diffusion recrystallization. Specifically, 101.91 mg of the black powder was weighed out and dissolved in DMF (20 mL). The solution was allowed to stand in a methanol atmosphere at room temperature in a dark place for about 2 weeks, thereby forming a precipitate of dark blue needle crystals (yield: 37.29 mg, 37%). The sample was analyzed for various physical properties. Hereinafter, the resulting compound is sometimes referred to as "Pd-Oqn."

Manufacturers and Product Numbers of Chemicals Used for Synthesis of the Complex D(+)-glucosamine hydrochloride: Wako, 073-02792
Potassium t-butoxide: Nacalai Tesque, 28536-82
8-hydroxy-2-quinolinecarbaldehyde: Wako, 352-12903
Sodium chloropalladate(II): Aldrich, 205818-25G Methanol (special grade): Nacalai, 21915-64

DMF (special grade): Nacalai, 13016-65

Silica gel: 60 (0.040 to 0.063 mm), Merck, 1.09385.1009

[Pd(GlcN=Oqn)Cl].0.5MeOH.1.5H$_2$O.(Pd-Oqn) Anal. Found (calcd for C$_{16.5}$H$_{22}$ClN$_2$O$_8$Pd) %: C, 38.37 (38.24); H, 3.90 (4.28); N, 5.42 (5.41).

FAB-MS m/z: [M-Cl]calcd for C$_{16}$H$_{17}$N$_2$O$_6$Pd, 439.0. found: 439.1.

Single-crystal X-ray structure analysis revealed that the dark-blue needle crystal contains two [Pd(GlcN=Oqn)Cl] molecules, one MeOH molecule, and three H$_2$O molecules in the asymmetric unit (Pd-Oqn=[Pd(GlcN=Oqn)Cl].0.5MeOH.1.5H$_2$O). In the complex, GlcN=Oqn is bound to Pd through three sites, i.e., N,N, and O, and forms, together with a Cl ion, a typical four-coordinate square planar geometry.

Single-crystal X-ray structure analysis and $^1$H NMR spectrum revealed that the glucosamine moiety of Pd-Oqn is in the conformation of β-$^4$C$_1$ both in crystal and in solution, and does not undergo conformational isomerization in solution. When the ligand GlcN=HOqn is not in the form of Pd-Oqn, isomerization occurs at the glucosamine moiety in solution, and $^1$H NMR spectroscopy revealed that α form:β form ratio is 20:80. This indicates that β form is thermodynamically more stable, and this property manifests more prominently when the ligand is in a complex form.

Synthesis Example 2

[Chem. 10]

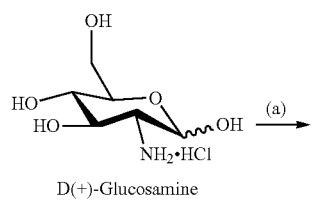

D(+)-Glucosamine Hydrochloride

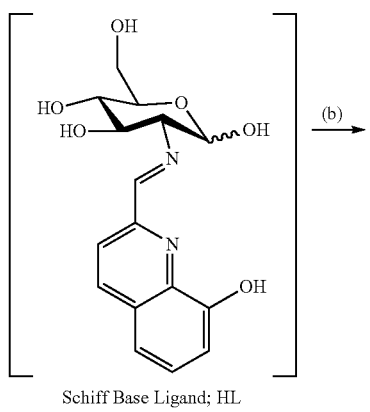

Schiff Base Ligand; HL

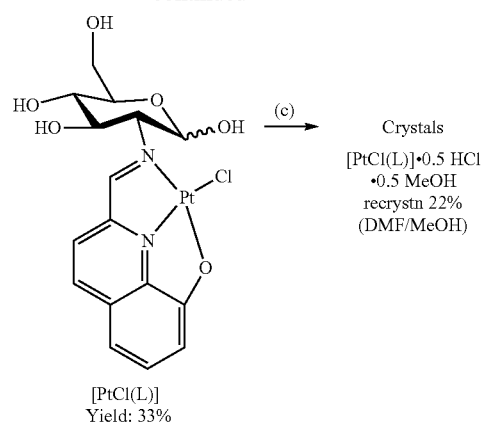

[PtCl(L)]
Yield: 33%

(a) tBuOK, 8-hydroxy-2-quinolinecarbaldehyde/MeOH
(b) i) Column chromatography (SiO$_2$, MeOH), ii) Pt(DMSO)$_2$Cl$_2$/MeOH
(c) recrystallization from DMF/MeOH Neutralization was carried out by adding D(+)-glucosamine hydrochloride (377.4 mg, 1.75 mmol) and potassium t-butoxide (196.4 mg, 1.75 mmol) to methanol (80 mL). Further, 8-hydroxy-2-quinolinecarbaldehyde (126.32 mg, 0.73 mmol) dissolved in methanol (40 mL) was added thereto, and the mixture was stirred at room temperature for 20 hours. After the completion of the reaction, the solvent was distilled off under reduced pressure and thereby concentrated to a volume of about 5 mL. The concentrate was developed by silica gel column chromatography (developing solvent: methanol), and the colored layers were all recovered. Subsequently, Pt(DMSO)$_2$Cl$_2$ (Non-patent Document 8) (700.9 mg, 1.66 mmol) was added to methanol (50 mL), and the mixture was heated to 60° C., followed by dropwise addition of the recovered methanol solution and stirring overnight, thereby forming a red precipitate (crude yield: 288.6 mg, 33%). The red powder was dissolved in DMF and allowed to stand in a methanol atmosphere for 2 weeks, thereby forming a precipitate of reddish brown needle crystals (yield: 209.9 mg, 22%).

Manufacturers and Product Numbers of Chemicals Used for Synthesis of the Complex D(+)-glucosamine hydrochloride: Wako, 073-02792

Potassium t-butoxide: Nacalai Tesque, 28536-82

Methanol (special grade): Nacalai, 21915-64

DMF (special grade): Wako, 045-02911

Silica gel: Fuji Silysia Chemical Ltd., PSQ100B

[Pt-Oqn=NGlc]$_2$.HCl.MeOH, Anal. Found: (calcd for C$_{33}$H$_{39}$Cl$_3$N$_4$O$_{13}$Pt$_2$): C, 32.92 (33.13), H, 3.24 (3.29), N, 4.96 (4.68)

Single-crystal X-ray structure analysis revealed that the precipitated reddish-brown needle crystal contains two [Pt-Oqn=NGlc] molecules, one MeOH molecule, and one HCl molecule in the asymmetric unit ([Pt-Oqn=NGlc].0.5HCl.0.5 MeOH). In the complex, GlcN=Oqn is bound to Pt through three sites, i.e., N,N, and O, and forms, together with a Cl ion, a typical four-coordinate square planar geometry.

Synthesis Example 3

The Production of the Following Compound

[Chem. 11]

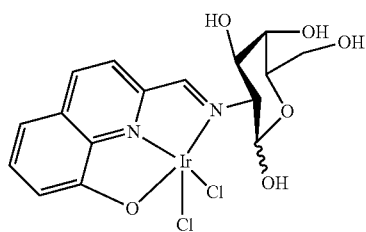

Neutralization was carried out by adding D(+)-glucosamine hydrochloride (52.0 mg, 0.24 mmol) and potassium t-butoxide (80.7 mg, 0.24 mmol) to methanol (15 mL). Further, 8-hydroxy-2-quinolinecarbaldehyde (41.5 mg, 0.24 mmol) dissolved in methanol (8 mL) was added thereto, and the mixture was stirred at room temperature for 20 hours. After the completion of the reaction, the solvent was distilled off under reduced pressure and thereby concentrated to a volume of about 5 mL. The concentrate was developed by silica gel column chromatography (developing solvent: methanol), and the colored layers were all recovered. Subsequently, $Na_3[IrCl_6]$ (99.2 mg, 0.22 mmol) was added to methanol (10 mL), and the mixture was heated to 60° C., followed by dropwise addition of the recovered methanol solution and stirring overnight. After the completion of the reaction, the solvent was distilled off under reduced pressure. Hereinafter, the resulting compound is sometimes referred to as "Ir-Oqn=NGlc."

Manufacturers and Product Numbers of Chemicals Used for Synthesis of the Complex
  D(+)-glucosamine hydrochloride: Wako, 073-02792
  Potassium t-butoxide: Nacalai Tesque, 28536-82
  $Na_3[IrCl_6]$: Strem Chemicals, 20197200
  Methanol (special grade): Nacalai, 21915-64
  DMF (special grade): Wako, 045-02911
  Silica gel: Fuji Silysia Chemical Ltd., PSQ100B
  Mass spectrometry (Ir-Oqn=NGlc): (as a chloride ion educt) ESI-TOF MS m/z found 526.1

Synthesis Example 4

The Production of the Following Compound

[Chem. 12]

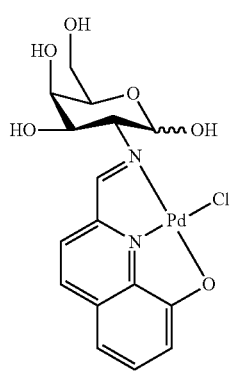

Neutralization was carried out by adding D(+)-galactosamine hydrochloride (13.0 mg, 0.060 mmol) and potassium t-butoxide (10.0 mg, 0.060 mmol) to methanol (5 mL). Further, 8-hydroxy-2-quinolinecarbaldehyde (10.4 mg, 0.060 mmol) dissolved in methanol (5 mL) was added thereto, and the mixture was stirred at room temperature for 20 hours. After the completion of the reaction, a white precipitate was removed by suction filtration. Subsequently, sodium chloropalladate(II) (17.7 mg, 0.060 mmol) was added to methanol (20 mL), and the above prepared methanol solution containing galactosamine hydrochloride and 8-hydroxy-2-quinolinecarbaldehyde was added thereto dropwise, followed by stirring at room temperature overnight. The resulting purple precipitate was recovered (yield: 11.7 mg, 42%). Hereinafter, the resulting compound is sometimes referred to as "Pd-Oqn=NGal."

Manufacturers and Product Numbers of Chemicals used for Synthesis of the Complex
  D(+)-galactosamine hydrochloride: Nacalai Tesque, 16510-14
  Potassium t-butoxide: Nacalai Tesque, 28536-82
  Methanol (special grade): Nacalai, 21915-64
  DMF (special grade): Wako, 045-02911
  Silica gel: Fuji Silysia Chemical Ltd., PSQ100B
  Mass spectrometry (Pd-Oqn=NGal): (as a chloride ion educt) ESI-TOF MS m/z found 439.0

Synthesis Example 5

The Production of the Following Compound

[Chem. 13]

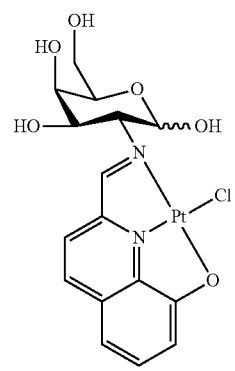

Neutralization was carried out by adding D(+)-galactosamine hydrochloride (13.0 mg, 0.060 mmol) and potassium t-butoxide (10.0 mg, 0.060 mmol) to methanol (5 mL). Further, 8-hydroxy-2-quinolinecarbaldehyde (10.4 mg, 0.060 mmol) dissolved in methanol (5 mL) was added thereto, and the mixture was stirred at room temperature for 20 hours. After the completion of the reaction, a white precipitate was removed by suction filtration. Subsequently, $Pt(DMSO)_2Cl_2$ (Non-patent Document 8) (25.3 mg, 0.060 mmol) was added to methanol (20 mL), and the mixture was heated to 60° C., followed by dropwise addition of the above prepared methanol solution containing galactosamine hydrochloride and 8-hydroxy-2-quinolinecarbaldehyde and stirring overnight. After the completion of the reaction, the solvent was distilled off under reduced pressure. Hereinafter, the resulting compound is sometimes referred to as "Pt-Oqn=NGal."

Manufacturers and Product Numbers of Chemicals Used for Synthesis of the Complex D(+)-galactosamine hydrochloride: Nacalai Tesque, 16510-14

Potassium t-butoxide: Nacalai Tesque, 28536-82

Methanol (special grade): Nacalai, 21915-64

DMF (special grade): Wako, 045-02911

Silica gel: Fuji Silysia Chemical Ltd., PSQ100B

Mass spectrometry (Pt-Oqn=NGal): (as a chloride ion educt) ESI-TOF MS m/z found 528.1

Synthesis Example 6

The Production of the Following Compound

[Chem. 14]

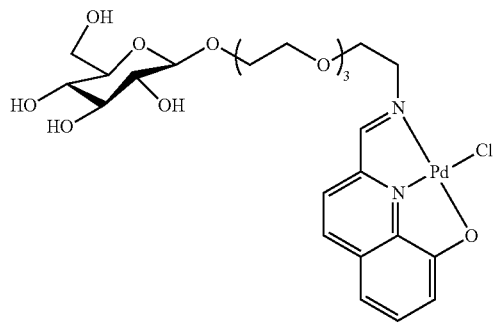

Glc-PEG-NH$_2$ (255.9 mg, 0.72 mmol) was dissolved in methanol (30 mL), and 8-hydroxy-2-quinolinecarbaldehyde (126.32 mg, 0.73 mmol) dissolved in methanol (20 mL) was added thereto, followed by stirring at room temperature for 20 hours. After the completion of the reaction, the solvent was distilled off under reduced pressure and thereby concentrated to a volume of about 5 mL. Subsequently, sodium chloropalladate(II) (202.76 mg, 0.67 mmol) dissolved in methanol (20 mL) was added to the above methanol solution containing Glc-PEG-NH$_2$ and 8-hydroxy-2-quinolinecarbaldehyde. After the completion of the reaction, the solvent was distilled off under reduced pressure. Hereinafter, the resulting compound is sometimes referred to as "Pd-Oqn=N-PEG-Glc."

Manufacturers and Product Numbers of Chemicals Used for Synthesis of the Complex Methanol (special grade): Nacalai, 21915-64

DMF (special grade): Wako, 045-02911

Silica gel: Fuji Silysia Chemical Ltd., PSQ100B

Mass spectrometry (Pd-Oqn=N-PEG-Glc): (as a chloride ion educt)

ESI-TOF MS m/z found 615.1

Text Example 1

Procedure of Anticancer Activity Test

1. Gastric cancer cell lines MKN28 and MKN45 were individually seeded in 96-well plates in duplicate at 1×10$^3$ cells/100 μL/well (a medium (RPMI1640) containing 10% FBS was used) and incubated at 37° C. and 5% CO$_2$ for 68 hours.

2. A preparation made by mixing a drug (CDDP ([PtCl$_2$(NH$_3$)$_2$]) or Pd-Oqn) with the medium was dispensed into each well, and thereafter incubated at 37° C. and 5% CO$_2$ for 48 hours.

3. MTT was dispensed into each well at 10 μL/well, followed by incubation at 37° C. for 4 hours. Thereafter, the absorbance at 450 nm was measured with a microplate reader, and the viability was calculated.

Results

FIGS. 1 to 4 show the results of the anticancer activity test. With respect to MKN45 (n=4), the IC$_{50}$ of CDDP was 28.2 μM, whereas that of Pd-Oqn was 11.7 μM. With respect to MKN28 (n=4), the IC$_{50}$ of CDDP was 87.2 μM, whereas that of Pd-Oqn was 17.5 μM. Thus, it was observed that Pd-Oqn exhibited extremely high anticancer activity (IC$_{50}$), about two to five times higher, against the stomach cancer cells (MKN45 and MKN28) than did cisplatin.

The results revealed that Pd-Oqn complex has excellent antitumor activity against stomach cancer cells MKN45 and MKN28.

Test Example 2

Procedure of Anticancer Activity Test

1. A pancreatic cancer cell line (Panc-1) was seeded in 96-well plates in duplicate at 1×10$^3$ cells/100 μL/well (a medium (RPMI1640) containing 10% FBS was used) and incubated at 37° C. and 5% CO$_2$ for 68 hours.

2. A preparation made by mixing a drug (CDDP ([PtCl$_2$(NH$_3$)$_2$]) or Pd-Oqn) with the medium was dispensed into each well, and thereafter incubated at 37° C. and 5% CO$_2$ for 48 hours.

3. MTT was dispensed into each well at 10 μL/well, followed by incubation at 37° C. for 4 hours. Thereafter, the absorbance at 450 nm was measured with a microplate reader, and the viability was calculated.

Results

Figure 5:
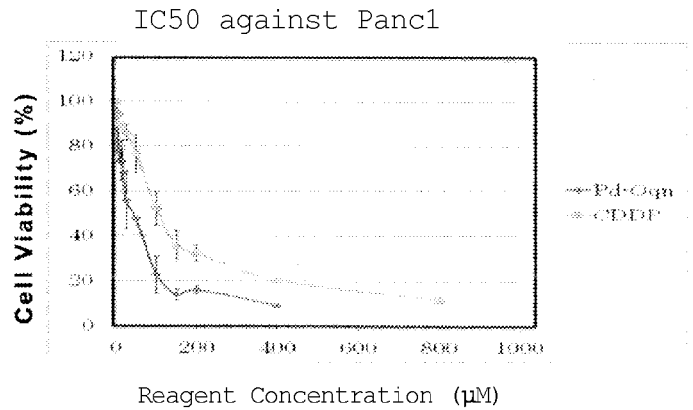
FIG. 5 is a graph showing the evaluation results of the toxicity of CDDP and Pd-Oqn to Panc-1.
Figure 6:
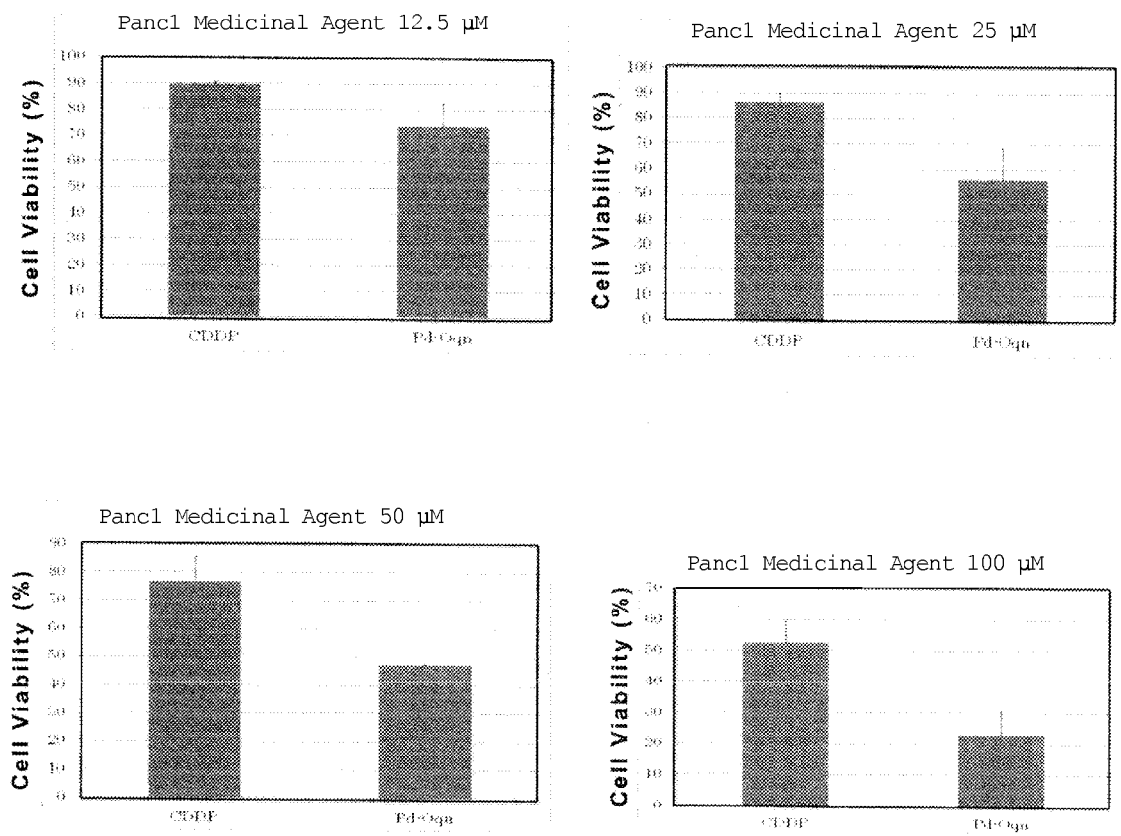
FIG. 6 is a graph showing the evaluation results of the toxicity of CDDP and Pd-Oqn to Panc-1.

FIGS. 5 and 6 show the results of the anticancer activity test. With respect to Panc-1 (n=4), the IC$_{50}$ of CDDP was 124.2 μM, whereas that of Pd-Oqn was 63.1 μM. Thus, Pd-Oqn exhibited high anticancer activity (IC$_{50}$), about two times higher, against the pancreatic cancer cell (Panc-1) than did cisplatin.

The results revealed that Pd-Oqn complex has excellent antitumor activity against pancreatic cancer cells.

The invention claimed is:

1. A pharmaceutical composition comprising as an active ingredient a compound represented by formula (I) or a physiologically acceptable salt thereof

[Chem. 1]

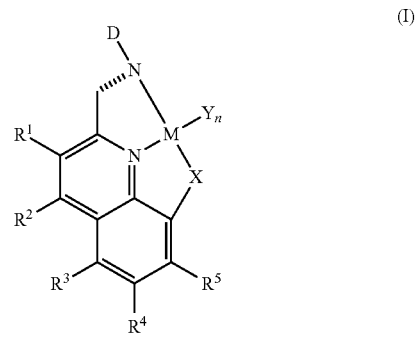

(I)

wherein the symbol "⦀" denotes a single bond "—" or a double bond "=";

R¹ to R⁵ are the same or different, and each represents hydrogen, alkyl, hydroxyalkyl, alkoxy, hydroxy, halogen, nitro, amino, a sugar residue, or a luminescent pigment;

M represents palladium, platinum, gold, iridium, or ruthenium;

X represents —O—, —NH$_2$—, —S—, —SH—, or —OSO$_2$—;

Y represents halogen or a long-chain fatty acid residue;

D represents a monosaccharide residue, an oligosaccharide residue, or a sugar-linked polyethylene glycol residue; and n represents an integer of 0 to 3.

2. The pharmaceutical composition according to claim 1, wherein R¹ to R⁵ represent hydrogen.

3. The pharmaceutical composition according to claim 1, wherein M is palladium or platinum.

4. The pharmaceutical composition according to claim 1, wherein D is a glucose residue, a galactose residue, or a mannose residue.

5. The pharmaceutical composition according to claim 1, wherein D is a D(+)-glucose residue.

6. The pharmaceutical composition according to claim 5, wherein the D(+)-glucose residue is a β-D(+)-glucose residue.

7. The pharmaceutical composition according to claim 1, wherein D is an L(−)-glucose residue.

8. The pharmaceutical composition according to claim 7, wherein the L(−)-glucose residue is a β-L(−)-glucose residue.

9. The pharmaceutical composition according to claim 1, wherein X is —O—.

10. The pharmaceutical composition according to claim 1, wherein Y is halogen.

11. The pharmaceutical composition according to claim 1, wherein the compound represented by formula (I) is a compound represented by formula (II)

[Chem. 2]

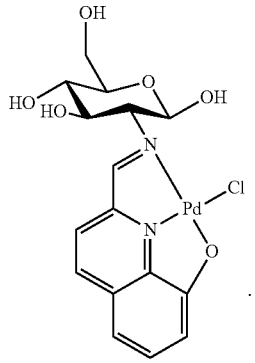

(II)

12. The pharmaceutical composition according to claim 1, which is an anticancer agent.

13. A method for treating cancer, the method comprising administering the compound represented by formula (I) or the physiologically acceptable salt thereof according to claim 1.

14. The pharmaceutical composition according to claim 1, wherein n is 1.

* * * * *